United States Patent
Marshall et al.

(10) Patent No.: US 11,839,438 B2
(45) Date of Patent: Dec. 12, 2023

(54) SURGICAL DRAPE

(71) Applicant: CMR SURGICAL LIMITED, Cambridge (GB)

(72) Inventors: Keith Marshall, Cambridge (GB); Nikki Priyam Su-Ling Phoolchund, Cambridge (GB); Thomas Bates Jackson, Cambridge (GB)

(73) Assignee: CMR SURGICAL LIMITED, Cambridge (GB)

( * ) Notice: Subject to any disclaimer, the term of this patent is extended or adjusted under 35 U.S.C. 154(b) by 1042 days.

(21) Appl. No.: 16/321,760

(22) PCT Filed: Jul. 27, 2017

(86) PCT No.: PCT/GB2017/052193
§ 371 (c)(1),
(2) Date: Jan. 29, 2019

(87) PCT Pub. No.: WO2018/020252
PCT Pub. Date: Feb. 1, 2018

(65) Prior Publication Data
US 2020/0352669 A1 Nov. 12, 2020

(30) Foreign Application Priority Data

Jul. 29, 2016 (GB) .................................. 1613093
Sep. 19, 2016 (GB) .................................. 1615918

(51) Int. Cl.
*A61B 46/17* (2016.01)
*A61B 46/00* (2016.01)
(Continued)

(52) U.S. Cl.
CPC .............. *A61B 34/30* (2016.02); *A61B 46/10* (2016.02); *A61B 46/17* (2016.02); *A61B 46/40* (2016.02);
(Continued)

(58) Field of Classification Search
CPC .......... A61B 17/29; A61B 2017/00477; A61B 2034/302; A61B 34/30; A61B 46/10; A61B 46/17; A61B 46/40; A61B 90/50
See application file for complete search history.

(56) References Cited

U.S. PATENT DOCUMENTS 8,506,555 B2   8/2013   Ruiz Morales
8,684,962 B2   4/2014   Kirschenman et al.
(Continued)

FOREIGN PATENT DOCUMENTS

CN   103702632 A   4/2014
CN   104411266 A   3/2015
(Continued)

OTHER PUBLICATIONS

English Translation of a Japanese Notification of Reasons for Refusal from corresponding Japanese Application No. 2019-504781 dated May 11, 2021.
(Continued)

*Primary Examiner* — Scott Luan
(74) *Attorney, Agent, or Firm* — Lando & Anastasi, LLP (57) ABSTRACT

A surgical drape for covering at least a portion of a surgical robot arm, the arm comprising at least one drive assembly interface element for transferring drive between the arm and an instrument engageable with the arm, the drape comprising an interface portion locatable between the arm and the instrument when the instrument is engaged with the arm; and a bulk portion encompassing the interface portion; the interface portion and the bulk portion being adjacent one another, the interface portion comprising one or more of a material or configuration having a lower modulus than that of the bulk portion in at least one direction, and a movable portion, the movable portion being movable relative to the
(Continued)

bulk portion, so as to permit repeatable movement of a portion of the interface portion relative to the bulk portion.

17 Claims, 8 Drawing Sheets

(51) Int. Cl.
    *A61B 34/30*           (2016.01)
    *A61B 90/50*           (2016.01)
    *A61B 46/10*           (2016.01)
    *A61B 17/00*           (2006.01)
    *A61B 17/29*           (2006.01)

(52) U.S. Cl.
    CPC .............. *A61B 90/50* (2016.02); *A61B 17/29* (2013.01); *A61B 2017/00477* (2013.01); *A61B 2034/302* (2016.02)

(56) References Cited

U.S. PATENT DOCUMENTS

| | | | |
|---|---|---|---|
| 9,568,992 | B2 | 2/2017 | Hasegawa et al. |
| 10,335,243 | B2 | 7/2019 | Yanagihara et al. |
| 10,603,126 | B2 | 3/2020 | Karguth et al. |
| 2003/0151721 | A1 | 8/2003 | Lai et al. |
| 2006/0052664 | A1 | 3/2006 | Julian et al. |
| 2006/0161138 | A1 | 7/2006 | Orban et al. |
| 2009/0248039 | A1 | 10/2009 | Cooper et al. |
| 2010/0170519 | A1 | 7/2010 | Romo et al. |
| 2010/0175701 | A1 | 7/2010 | Reis et al. |
| 2011/0168189 | A1* | 7/2011 | Cooper .................. A61B 34/30 128/849 |
| 2011/0277775 | A1 | 11/2011 | Holop et al. |
| 2012/0289973 | A1 | 11/2012 | Prisco et al. |
| 2013/0317519 | A1 | 11/2013 | Romo et al. |
| 2014/0001234 | A1 | 1/2014 | Shelton, IV et al. |
| 2014/0001235 | A1 | 1/2014 | Shelton, IV |
| 2015/0148818 | A1 | 5/2015 | Lohmeier et al. |
| 2015/0173726 | A1 | 6/2015 | Lohmeier et al. |
| 2015/0173731 | A1 | 6/2015 | Lohmeier et al. |
| 2015/0202009 | A1* | 7/2015 | Nussbaumer .......... A61B 46/27 128/856 |
| 2015/0257841 | A1 | 9/2015 | Dachs, II |
| 2016/0058513 | A1 | 3/2016 | Giorgi et al. |
| 2016/0151120 | A1 | 6/2016 | Kostrzewski et al. |

FOREIGN PATENT DOCUMENTS

| | | |
|---|---|---|
| CN | 105163685 A | 12/2015 |
| CN | 105640647 A | 6/2016 |
| EP | 2886061 A2 | 6/2015 |
| GB | 2538230 A | 11/2016 |
| JP | 2009525098 A | 7/2009 |
| JP | 2012055377 A | 3/2012 |
| JP | 2013027733 A | 2/2013 |
| JP | 2013530738 A | 8/2013 |
| JP | 2015523147 A | 8/2015 |
| JP | 2016120277 A | 7/2016 |
| JP | 2019512319 A | 5/2019 |
| JP | 2019523071 A | 8/2019 |
| WO | 2007041093 A1 | 4/2007 |
| WO | 2009061915 A2 | 5/2009 |
| WO | 2010081050 A1 | 7/2010 |
| WO | 2011037394 A2 | 3/2011 |
| WO | 2015057821 A1 | 4/2015 |
| WO | 2015142793 A1 | 9/2015 |
| WO | 2016081286 A1 | 5/2016 |
| WO | 2016090459 A1 | 6/2016 |
| WO | 2016097861 A1 | 6/2016 |
| WO | 2017015167 A1 | 1/2017 |
| WO | 2017158263 A1 | 9/2017 |
| WO | 2018020252 A2 | 2/2018 |
| WO | 2018020254 A2 | 2/2018 |

OTHER PUBLICATIONS

Japanese Notification of Reasons for Refusal from corresponding Japanese Patent Application No. 2019-054794 dated Jun. 15, 2021 [English translation attached].
English Translation of a Chinese First Notification of Office Action from corresponding Chinese Application No. 201780047136.X dated Jan. 13, 2021.
Indian Examination Report from corresponding Indian Application No. 201917007380 dated Apr. 30, 2021.
United Kingdom Examination Report from corresponding United Kingdom Application No. GB1613093.2 dated Mar. 22, 2021.
International Search Report and Written Opinion from corresponding PCT/GB2017/052192 dated Oct. 30, 2017.
Notification of Transmittal of the International Search Report and the Written Opinion of the International Searching Authority from corresponding PCT/GB2017/052193 dated Jan. 30, 2018.
Notification of Transmittal of the International Search Report and the Written Opinion of the International Searching Authority from corresponding PCT/GB2017/052195 dated Jan. 30, 2018.
United Kingdom Search Report from corresponding United Kingdom Application No. GB1613093.2 dated Jan. 27, 2017.
United Kingdom Search Report from corresponding United Kingdom Application No. GB1615615.0 dated Feb. 16, 2017.
United Kingdom Search Report from corresponding United Kingdom Application No. GB1615616.8 dated Feb. 22, 2017.
United Kingdom Search Report from corresponding United Kingdom Application No. GB1615918.8 dated Feb. 16, 2017.
United Kingdom Search Report from corresponding United Kingdom Application No. GB1615919.6 dated Feb. 23, 2017.
English Translation of a Japanese Notification of Reasons for Refusal from corresponding Japanese Patent Application No. 2019-504801 dated May 13, 2021.
United Kingdom Search Report from corresponding United Kingdom Application No. GB2114611.2 dated Nov. 18, 2021.
Japanese Notification of Reasons for Refusal from corresponding Japanese Application No. 2021-214509 dated Dec. 13, 2022.
Japanese Notification of Reasons for Refusal from corresponding Japanese Application No. 2022-012276 dated Dec. 6, 2022.
Japanese Decision to Grant a Patent from corresponding Japanase Patent Application No. 2019504801 dated Jun. 23, 2022.

* cited by examiner

SURGICAL DRAPE

CROSS-REFERENCE TO RELATED APPLICATIONS

This application is a U.S. National Phase Application under 35 U.S.C. § 371 of International Application No. PCT/GB2017/052193, filed Jul. 27, 2017, which claims priority to United Kingdom Application No. 1613093.2, filed Jul. 29, 2016 and United Kingdom Application No. 1615918.8, filed Sep. 19, 2016, all of which are hereby incorporated by reference in their entireties for all purposes.

BACKGROUND

Figure 1:
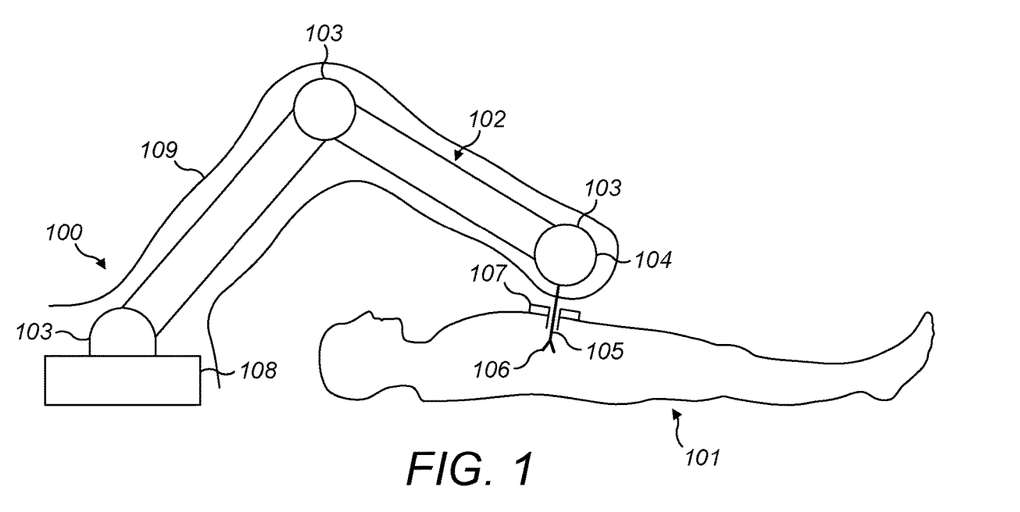
FIG. 1 illustrates a surgical robot performing a surgical procedure.

It is known to use robots for assisting and performing surgery. FIG. 1 illustrates a surgical robot 100 which consists of a base 108, an arm 102, and an instrument 105 comprising an end effector 106. The base supports the robot, and is itself attached rigidly to, for example, the operating theatre floor, the operating theatre ceiling or a trolley. The arm extends between the base and the instrument. The arm is articulated by means of multiple flexible joints 103 along its length, which are used to locate the surgical instrument in a desired location relative to the patient 101. The surgical instrument is attached to the distal end 104 of the robot arm. The surgical instrument penetrates the body of the patient 101 at a port 107 so as to access the surgical site. At its distal end, the instrument comprises an end effector 106 for engaging in a medical procedure.

The robotic arm 102 is shrouded by a surgical drape 109 to provide a sterile boundary between the surgical instrument (which must be sterile) and the robotic arm (which may not be sterile). The drape provides a boundary between the robotic arm and the sterile field in which the arm is positioned (for example an operating theatre).

Figure 2:
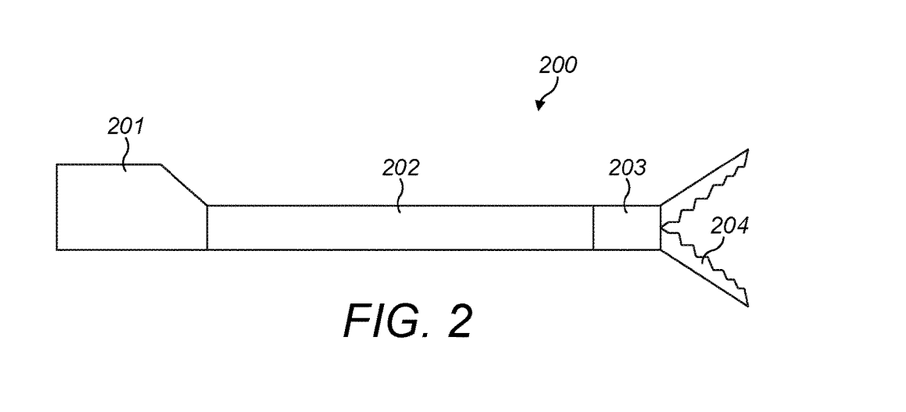
FIG. 2 illustrates an end effector for use with the surgical robot illustrated in FIG. 1.

FIG. 2 illustrates a surgical instrument 200 for performing robotic laparoscopic surgery. The surgical instrument comprises an instrument base 201 by means of which the surgical instrument connects to the robot arm. A shaft 202 extends between the instrument base 201 and an articulation 203. The articulation 203 terminates in an end effector 204. In FIG. 2, a pair of serrated jaws are illustrated as the end effector 204. The articulation 203 permits the end effector 204 to move relative to the shaft 202. It is desirable for at least two degrees of freedom to be provided to the motion of the end effector 204 by means of the articulation.

The articulation 203 may be mechanically driven by a drive assembly powered by one or more motors housed within the robot arm rather than in the instrument. Mechanical drive needs to be connected, or coupled, to the instrument through the surgical drape.

The connection of the mechanical drive through the surgical drape presents difficulties when attempting to maintain the sterile barrier provided by the drape. There is a need for an improved surgical drape.

SUMMARY

According to an aspect of the invention there is provided a surgical drape for covering at least a portion of a surgical robot arm, the arm comprising at least one drive assembly interface element for transferring drive between the arm and an instrument engageable with the arm, the drape comprising:

an interface portion locatable between the arm and the instrument when the instrument is engaged with the arm; and a bulk portion encompassing the interface portion; the interface portion and the bulk portion being adjacent one another, the interface portion comprising one or more of a material or configuration having a lower modulus than that of the bulk portion in at least one direction, and a movable portion, the movable portion being movable relative to the bulk portion, so as to permit repeatable movement of a portion of the interface portion relative to the bulk portion.

Suitably the bulk portion wholly encompasses the interface portion. Suitably the material of the interface portion is at least one of a woven and a resilient material. Suitably the interface portion comprises an unconstrained portion of the drape.

Suitably the interface portion comprises a ruckle control portion configured to at least partially control tension in the material of the drape. Suitably the ruckle control portion comprises the movable portion.

Suitably the ruckle control portion comprises a concertina section, the concertina section being configurable between an expanded state and a contracted state.

Suitably the concertina section is biased towards one of the expanded state and the contracted state.

Suitably the ruckle control portion comprises a reel for at least one of winding on and unwinding material of the movable portion. Suitably the reel is at least one of biased and drivable in a rotary direction.

Suitably the ruckle control portion comprises a strengthened portion, the strengthened portion being configured to permit a preferential deformation of the interface portion under action of a force. Suitably the strengthened portion forms at least part of a periphery of a non-strengthened portion.

Suitably the drape is configured to engage with a plurality of drive assembly interface elements, and the drape comprises a ruckle control portion corresponding to each of the plurality of drive assembly interface elements.

Suitably the interface portion comprises a drive transfer element engageable with the drive assembly interface element. Suitably the drive transfer element comprises portions attached to either side of the drape.

Suitably the movable portion comprises a first drape portion and a second drape portion, the first drape portion and the second drape portion being releasably engageable with one another along a joining line such that a gap between the first drape portion and the second drape portion is movable along the joining line.

Suitably the drape comprises a sensor for sensing at least one of tension in the drape and force on the drape.

According to another aspect of the present invention, there is provided a surgical system comprising a surgical drape as defined above, a control unit and a sensor; the sensor being configured to sense at least one of tension in the drape and force on the drape and to transmit a signal to the control unit, and the control unit being configured to determine at least one of the tension in the drape and the force on the drape in dependence on the signal.

Any one or more feature of any aspect above may be combined with any one or more feature of any other aspect above. Any apparatus feature may be written as a method feature where possible, and vice versa. These have not been written out in full here merely for the sake of brevity.

This Summary is provided to introduce a selection of concepts in a simplified form that are further described below in the Detailed Description. The mention of features in this Summary does not indicate that they are key features or essential features of the invention or of the claimed subject matter, nor is it to be taken as limiting the scope of the claimed subject matter.

BRIEF DESCRIPTION OF THE DRAWINGS

The present invention will now be described by way of example with reference to the accompanying drawings. In the drawings:

FIG. 7b schematically illustrates a plan view of the ruckle control portion shown in FIG. 7a;

DETAILED DESCRIPTION

Figure 3:
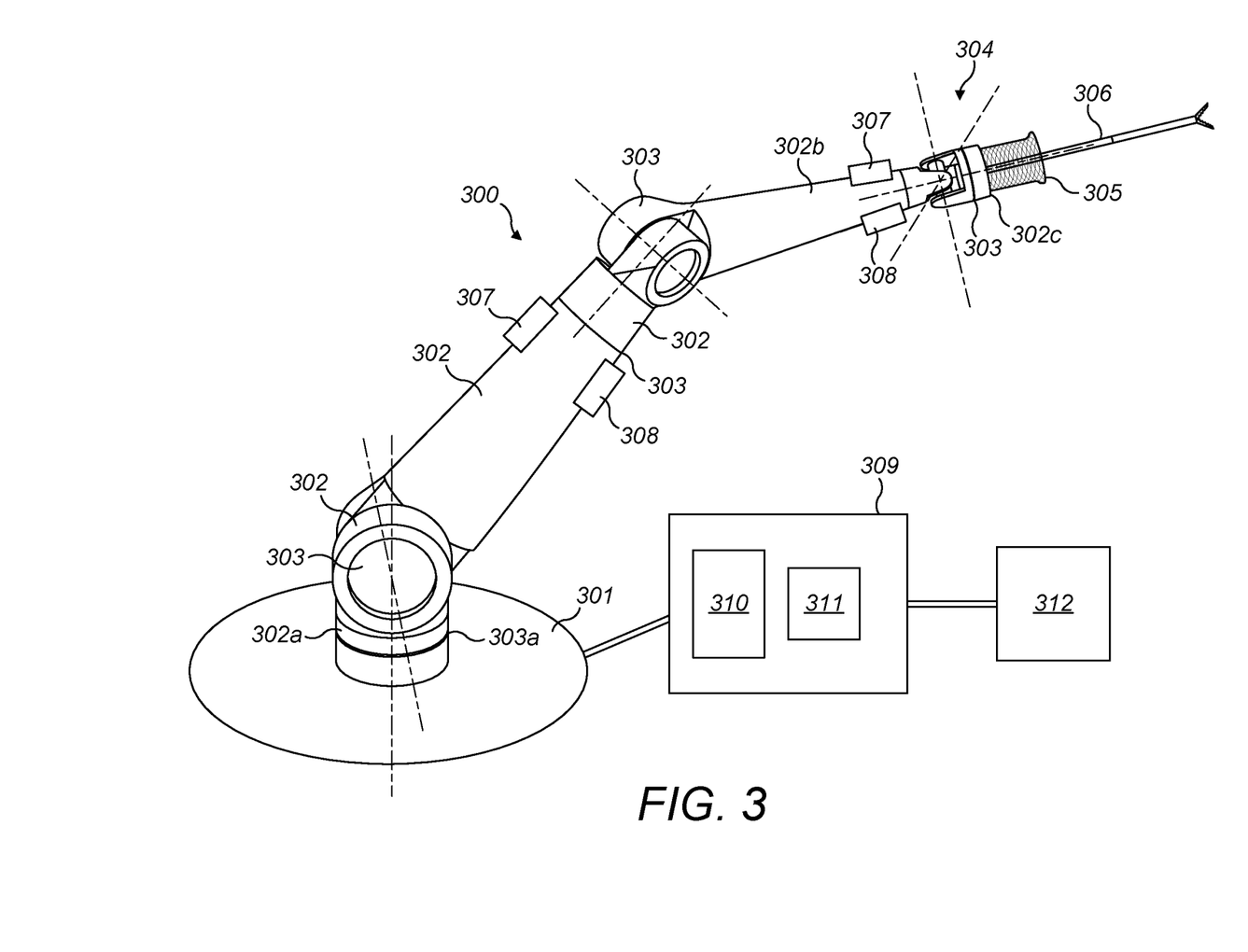
FIG. 3 illustrates a surgical robot.

FIG. 3 illustrates a surgical robot having an arm 300 which extends from a base 301. The arm comprises a number of rigid limbs 302. The limbs are coupled by revolute joints 303. The most proximal limb 302a is coupled to the base by a proximal joint 303a. It and the other limbs are coupled in series by further ones of the joints 303. Suitably, a wrist 304 is made up of four individual revolute joints. The wrist 304 couples one limb (302b) to the most distal limb (302c) of the arm. The most distal limb 302c carries an attachment 305 for a surgical instrument 306. Each joint 303 of the arm has one or more motors 307 which can be operated to cause rotational motion at the respective joint, and one or more position and/or torque sensors 308 which provide information regarding the current configuration and/or load at that joint. Suitably, the motors are arranged proximally of the joints whose motion they drive, so as to improve weight distribution. For clarity, only some of the motors and sensors are shown in FIG. 3. The arm may be generally as described in our co-pending patent application PCT/GB2014/053523.

The arm terminates in the attachment 305 for interfacing with the instrument 306. Suitably, the instrument 306 takes the form described with respect to FIG. 2. The instrument has a diameter less than 8 mm. Suitably, the instrument has a 5 mm diameter. The instrument may have a diameter which is less than 5 mm. The instrument diameter may be the diameter of the shaft. The instrument diameter may be the diameter of the profile of the articulation. Suitably, the diameter of the profile of the articulation matches or is narrower than the diameter of the shaft. The attachment 305 comprises a drive assembly for driving articulation of the instrument. Movable interface elements of the drive assembly interface mechanically engage corresponding movable interface elements of the instrument interface in order to transfer drive from the robot arm to the instrument. One instrument is exchanged for another several times during a typical operation. Thus, the instrument is attachable to and detachable from the robot arm during the operation. Features of the drive assembly interface and the instrument interface aid their alignment when brought into engagement with each other, so as to reduce the accuracy with which they need to be aligned by the user.

The instrument 306 comprises an end effector for performing an operation. The end effector may take any suitable form. For example, the end effector may be smooth jaws, serrated jaws, a gripper, a pair of shears, a needle for suturing, a camera, a laser, a knife, a stapler, a cauteriser, a suctioner. As described with respect to FIG. 2, the instrument comprises an articulation between the instrument shaft and the end effector. The articulation comprises several joints which permit the end effector to move relative to the shaft of the instrument. The joints in the articulation are actuated by driving elements, such as cables. These driving elements are secured at the other end of the instrument shaft to the interface elements of the instrument interface. Thus, the robot arm transfers drive to the end effector as follows: movement of a drive assembly interface element moves an instrument interface element which moves a driving element which moves a joint of the articulation which moves the end effector.

Controllers for the motors, torque sensors and encoders are distributed within the robot arm. The controllers are connected via a communication bus to a control unit 309. The control unit 309 comprises a processor 310 and a memory 311. The memory 311 stores in a non-transient way software that is executable by the processor to control the operation of the motors 307 to cause the arm 300 to operate in the manner described herein. In particular, the software can control the processor 310 to cause the motors (for example via distributed controllers) to drive in dependence on inputs from the sensors 308 and from a surgeon command interface 312. The control unit 309 is coupled to the motors 307 for driving them in accordance with outputs generated by execution of the software. The control unit 309 is coupled to the sensors 308 for receiving sensed input from the sensors, and to the command interface 312 for receiving input from it. The respective couplings may, for example, each be electrical or optical cables, or may be provided by a wireless connection. The command interface 312 comprises one or more input devices whereby a user can request motion of the end effector in a desired way. The input devices could, for example, be manually operable mechanical input devices such as control handles or joysticks, or contactless input devices such as optical gesture sensors. The software stored in the memory 311 is configured to respond to those inputs and cause the joints of the arm and instrument to move accordingly, in compliance with a predetermined control strategy. The control strategy may include safety features which moderate the motion of the arm and instrument in response to command inputs. Thus, in summary, a surgeon at the command interface 312 can control the instrument 306 to move in such a way as to perform a desired surgical procedure. The control unit 309 and/or the command interface 312 may be remote from the arm 300.

Figure 4:
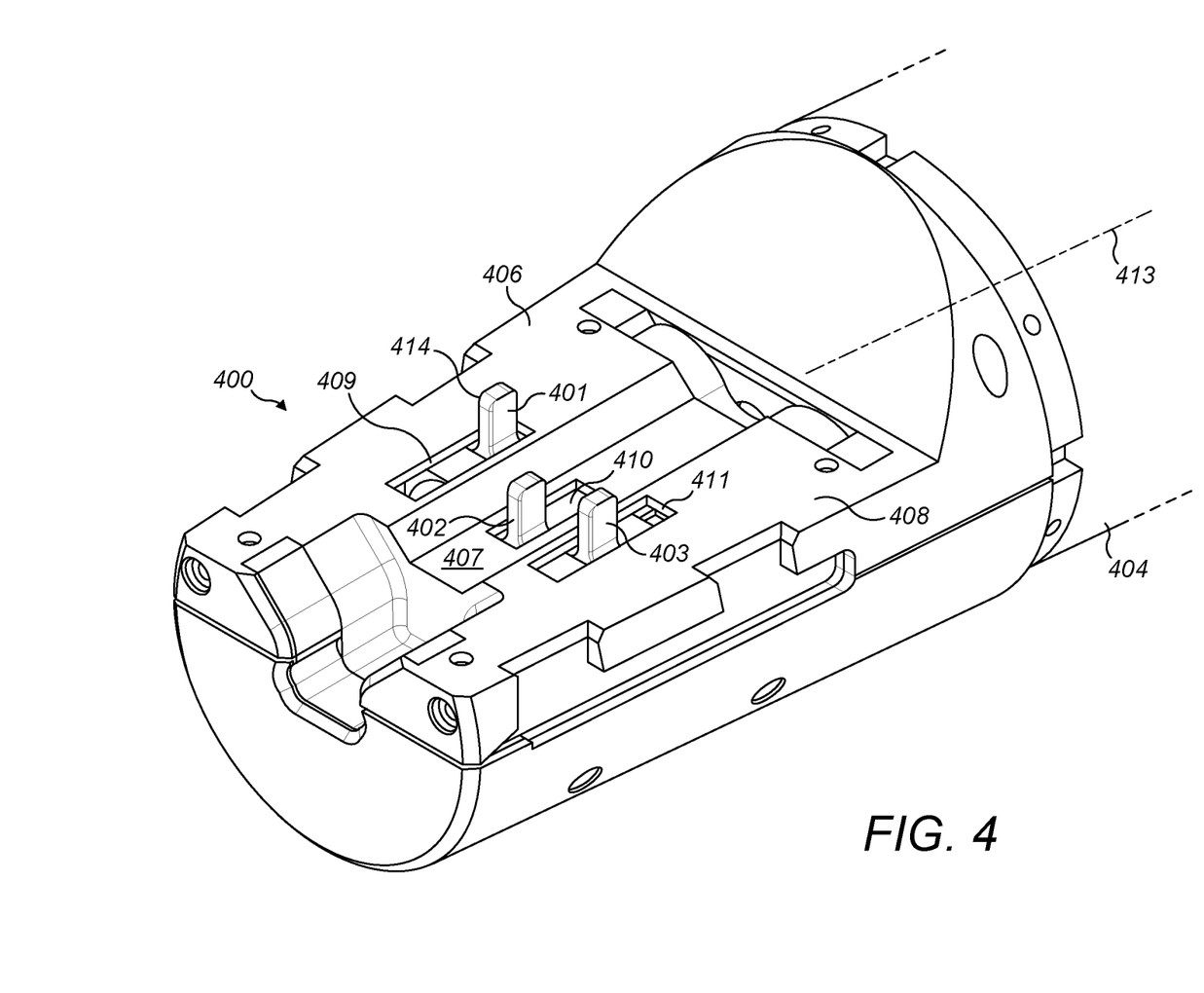
FIG. 4 illustrates a drive assembly interface of a surgical robot arm.
Figure 5:
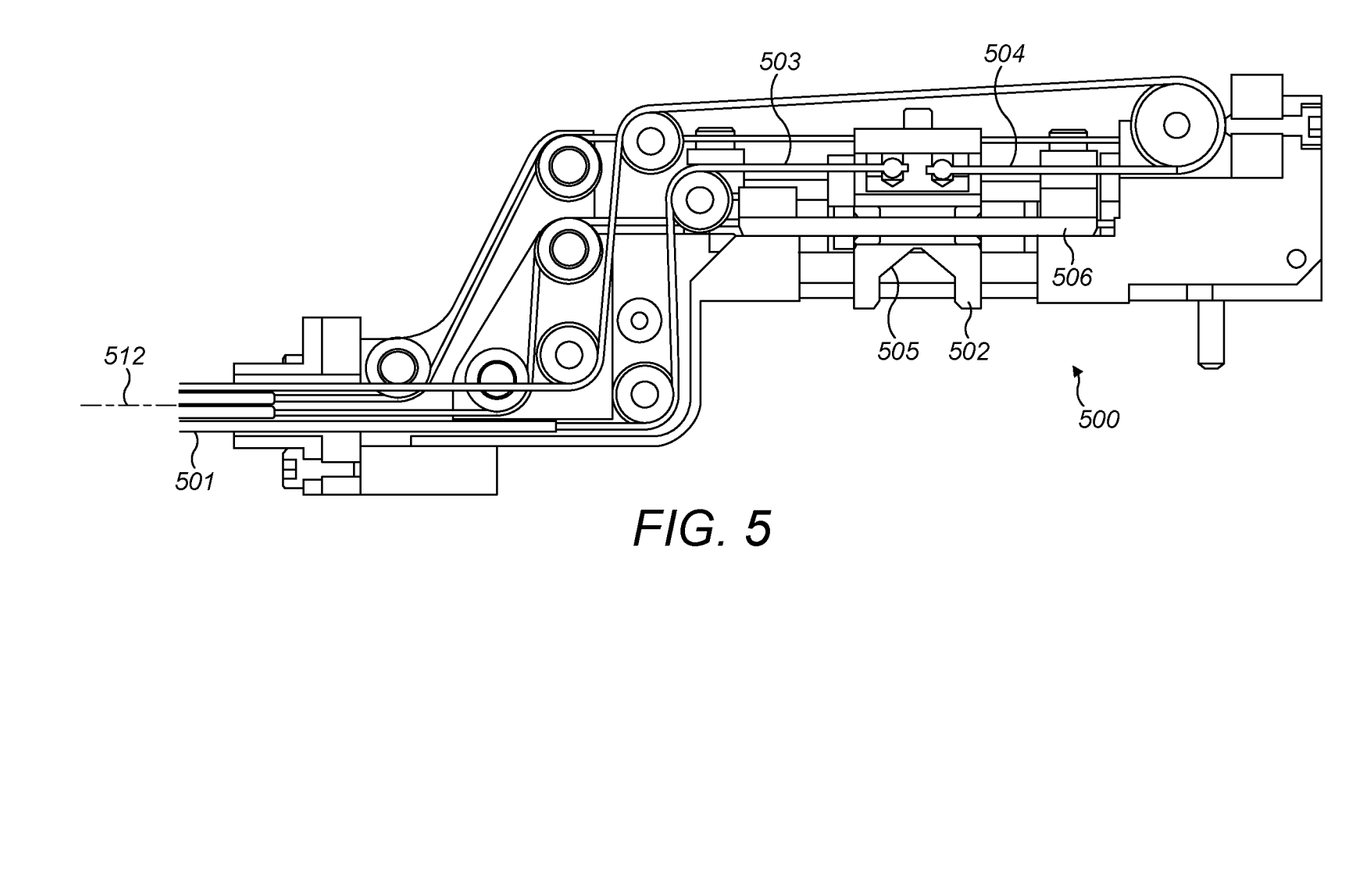
FIG. 5 illustrates an instrument interface of a surgical instrument.

FIGS. 4 and 5 illustrate an exemplary mechanical interconnection of the drive assembly interface and the instrument interface in order to transfer drive from the robot arm to the instrument. FIG. 4 illustrates an exemplary drive assembly interface 400 at the end of a robot arm 404. The drive assembly interface 400 comprises a plurality of drive assembly interface elements 401, 402, 403. The drive assembly interface elements protrude from surfaces 406, 407, 408 on the drive assembly interface 400. The protrusion of the drive assembly interface elements from the drive assembly interface 400 permits engagement of the drive assembly interface elements with corresponding instrument interface elements, as described below. The protrusions are in the form of fins in the illustrated example. In other implementations, other types of protrusion can be provided. The drive assembly interface elements suitably comprise a stiff material, such as a metal. Suitably the protrusion is formed from a stiff material, such as a metal. Preferably the drive assembly interface element is formed from a stiff material, such as a metal.

The protrusions (the fins in the illustrated example) comprise a chamfer 414 at their distal ends. The chamfer provides for ease of engagement of the protrusions in corresponding recesses, as described below. In other examples the distal ends of the protrusions can be provided with a rounded corner. The edges of the chamfered portions can be rounded.

The fins extend through the surfaces 406, 407, 408. The portions of the fins that protrude from the surfaces are perpendicular to the plane of the surfaces. In other examples the fins can protrude in a direction that is within a range of 10 degrees from perpendicular. Preferably the direction in which the fins extend is within a range of 5 degrees or within a range of 2 degrees from perpendicular.

FIG. 4 illustrates three drive assembly interface elements. In other examples, there may be greater than or fewer than three drive assembly interface elements. The drive assembly interface elements 401, 402, 403 are movable within the drive assembly interface 400 along linear paths 409, 410, 411. The paths can be parallel with one another. Suitably at least two of the paths are parallel. The paths need not be precisely parallel with one another. There may be some tolerance in how closely aligned the paths need to be. For example, the paths may be within 10 degrees of each other. The paths may extend in respective directions within a 10 degree range. Preferably the paths are within 5 degrees of each other, or within 2 degrees or 1 degree of each other. The paths may extend in respective directions within a 5 degree range, or preferably a 2 degree or 1 degree range.

Aligning the paths in this manner can assist in providing corresponding mechanisms more compactly. For instance, the mechanisms can be arranged to move alongside one another, permitting the mechanisms to be arranged more closely together.

In the illustrated example, the linear paths 409, 410, 411 are disposed on two parallel planes. The central linear path 410 is disposed on a plane 407 set into the drive assembly interface 400 compared to that in which the outer two linear paths 409, 411 are disposed. This arrangement permits a more compact interface between the drive assembly interface 400 and an instrument interface 500.

In other implementations, the three linear paths 409, 410, 411 can be disposed on the same plane, or all on different planes. In another example, the outer two linear paths 409, 411 are disposed on a plane set into the drive assembly interface 400 compared to that in which the central linear path 410 is disposed. In implementations utilising differing numbers of drive assembly interface elements, different configurations of planes on which the paths are disposed are possible.

Referring now to FIG. 5, the shaft 501 of the instrument terminates in the instrument interface 500. The instrument interface 500 comprises a plurality of instrument interface elements (one of which is shown at 502 in FIG. 5). The instrument interface elements suitably comprise a stiff material, such as a metal. Suitably the instrument interface element is formed from a stiff material, such as a metal. Pairs of driving elements (one such pair is shown at 503, 504) extend into the instrument interface 500 from the end of the shaft 501. Each pair of driving elements terminates in one of the instrument interface elements. In the example shown in FIG. 5, the driving element pair 503, 504 terminates in instrument interface element 502; likewise, other driving element pairs terminate in corresponding instrument interface elements.

In the illustrated example there are three driving element pairs that terminate in three instrument interface elements. In other examples, there may be greater than or fewer than three instrument interface elements. There may be greater than or fewer than three driving element pairs. In FIG. 5 there is a one-to-one relationship between instrument interface elements and driving element pairs. In other examples, there may be any other coupling relationship between the instrument interface elements and driving element pairs. For example, a single instrument interface element may drive more than one pair of driving elements. In another example, more than one instrument interface element may drive a single pair of driving elements.

Each instrument interface element 502 comprises a recess, or cup 505, which is the portion of the instrument interface element engageable with the drive assembly interface element.

The instrument interface elements are displaceable within the instrument interface. In the example shown, the instrument interface elements are slideable along rails. Instrument interface element 502 is slideable along rail 506. Each instrument interface element is displaceable along a direction parallel to the direction of elongation of the pair of driving elements which that instrument interface element holds captive. Each instrument interface element is displaceable in a direction parallel to the longitudinal axis 512 of the instrument shaft 501. When the instrument interface element moves along its respective rail, it causes a corresponding movement to the driving element pair secured to it. Thus, moving an instrument interface element drives motion of a driving element pair and hence motion of a joint of the instrument.

Drive assembly interface 400 mates with instrument interface 500. The instrument interface 500 comprises structure for receiving the drive assembly interface elements 401, 402, 403. Specifically, the instrument interface elements receive the drive assembly interface elements. In the example shown, each instrument interface element comprises a socket or cup 505 for receiving the fin of the corresponding drive assembly interface element. The socket 505 of one instrument interface element 502 receives a fin of the corresponding drive assembly interface element 402. Similarly, sockets of the other instrument interface elements receive fins of the other drive assembly interface elements.

Each drive assembly interface element is displaceable within the drive assembly. This displacement is driven. For example, the displacement may be driven by a motor and lead screw arrangement.

Each drive assembly interface element is displaceable along a direction parallel to the longitudinal axis 413 of the terminal link of the robot arm. When the drive assembly interface element moves, it causes a corresponding movement to the instrument interface element to which it is engaged. Thus, driving motion of a drive assembly interface element drives motion of an instrument interface element which drives articulation of the end effector of the instrument.

The portions of the fins that protrude from the surfaces comprise front and rear faces aligned in the directions of movement of the drive assembly interface elements. Here, front and rear refer to movement in one direction, when the front face will face the direction of movement and the rear face will face away from the direction of movement. When the drive assembly interface element moves in the opposite direction, the front face will face away from the direction of movement and the rear face will face the direction of movement.

The front and rear faces of the drive assembly interface elements are transverse to the direction in which the drive assembly interface elements are drivably movable. The front and rear faces of the drive assembly interface elements are parallel to the direction in which the fins protrude from the surfaces. The front and rear faces need not be exactly parallel to this direction, but are preferably within a range of 10 degrees, or within a range of 5 degrees, or more preferably within a range of 2 degrees of this direction.

The socket 505 comprises an interior face that is transverse to the direction in which the instrument interface elements are movable. The interior face need not be exactly transverse to this direction, but is preferably within a range of 10 degrees, or within a range of 5 degrees, or more preferably within a range of 2 degrees of being transverse to this direction.

In the illustrated example the interior face of the instrument interface elements and the front and rear faces of the drive assembly interface elements are parallel to one another. This can assist in the transferal of drive between the elements.

On engagement of the instrument interface 500 with the drive assembly interface 400, the drive assembly interface elements are held captive by respective instrument interface elements. The instrument interface elements and the drive assembly interface elements are all displaceable in the same direction. This direction is parallel to both the longitudinal axis 413 of the terminal link of the robot arm 404 and the longitudinal axis 512 of the instrument shaft 501.

Thus, in the illustrated example, linear drive is transferred between the drive assembly 400 and the instrument. In other examples, the drive need not be linear drive. For instance, the drive could be rotational drive, or drive about an arc.

Figure 6A:
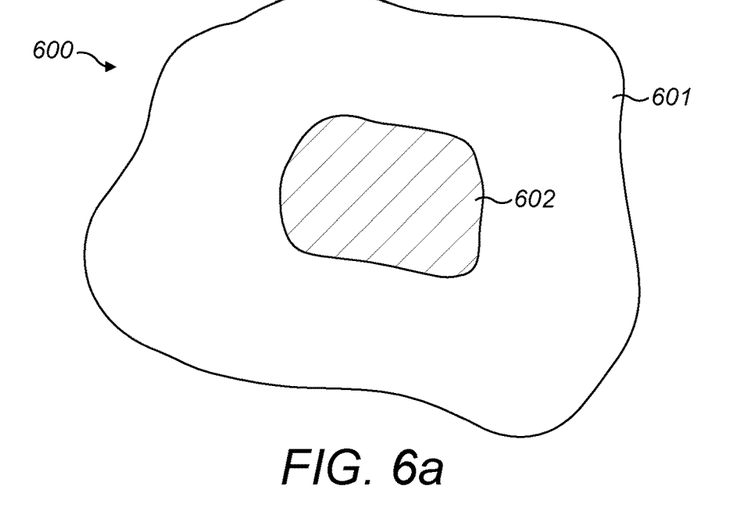
FIGS. 6a, 6b and 6c illustrate a portion of a surgical drape.

During an operation or surgical procedure, the surgical robot is shrouded in a sterile drape (an example of which is illustrated in FIG. 6a) to provide a sterile barrier between the non-sterile surgical robot and the sterile operating environment. The portion of the robot that is covered by the drape then need not be sterile. The surgical instrument is sterilised before being attached to the surgical robot. The sterile drape is typically constructed of a plastic sheet, for example made of polyester, polypropylene, polyethylene or polytetrafluoroethylene (PTFE). Suitably, the drape is flexible and/or deformable. This can assist in the drape shrouding the robot arm without interfering in the location and/or movement of the robot arm and/or instruments during the surgical procedure.

The sterile drape 600 suitably passes between the drive assembly interface 400 and the instrument interface 500. To maintain a sterile barrier between the instrument (which will have been sterilised for use in a surgical procedure) and the robot arm (which typically will not be sterile), the surgical drape is provided between the drive assembly interface 400 and the instrument interface 500. Engagement of the instrument interface 500 with the drive assembly interface 400 will capture a portion of the drape that is between the instrument interface 500 and the drive assembly interface 400.

The sterile drape forms a barrier between the drive assembly and the instrument interface. This barrier need not be completely hermetic, but is suitably substantially hermetic.

The engagement between the fins and sockets, or more generally between the drive assembly interface elements and the instrument interface elements, is made through the captured portion of the drape. Suitably the captured portion permits movement of the drive assembly interface elements and instrument interface elements relative to the drive assembly and instrument interface so as to transfer drive, but without such movement adversely affecting the integrity of the drape. Maintaining the integrity of the drape ensures that the sterile barrier is not compromised.

In the illustrated example, the drive assembly interface elements comprise protrusions (i.e. fins) and the instrument interface elements comprise recesses (i.e. sockets). In some examples the instrument interface elements can comprise the protrusions and the drive assembly interface elements can comprise the recesses. In other examples, combinations are possible: one or more drive assembly interface element can comprise a protrusion and another one or more drive assembly interface element can comprise a recess, and a corresponding one or more instrument interface element can comprise a recess and another one or more instrument interface element can comprise a protrusion.

The engagement between a protrusion and a recess will potentially cause a drape held taut between the instrument interface and the drive assembly interface to rip or tear, or otherwise rupture, thus potentially compromising the sterile barrier. Even if the drape does not immediately rip or tear, the movement of the drive assembly interface elements when transferring drive can cause the drape to rip or tear, or otherwise rupture. The sterile barrier may additionally or alternatively be compromised by the drape being thinned, or worn away, over time as well as by the drape rupturing. The provision of the chamfer 414 and/or rounding towards the end of the protrusions can reduce the likelihood of damage occurring to the drape when captured between a protrusion and a recess.

In addition to the possibility of tearing the drape, a deformation of the drape can cause a force on one or more interface element that might affect the interface element, such as by affecting its movement. This can impair the performance of the interface, or of the robot as a whole. For example, the force on the interface element caused by the drape can restrict free movement of the interface element under action of drive provided by the drive assembly. The force on the interface element caused by the drape can also affect force feedback measurements which might sense forces on one or more interface element. Thus the forces caused by the drape might introduce inaccuracies in such force feedback measurements.

To avoid or restrict the sterile barrier being compromised, the drape is provided with an interface portion 602, as illustrated in FIG. 6a. The captured portion can comprise the interface portion. The interface portion 602 is shown as being surrounded or encompassed by a bulk portion 601 of the drape. Suitably the bulk portion wholly surrounds the interface portion. The bulk portion is provided adjacent the interface portion. Suitably the bulk portion abuts or adjoins the interface portion. Suitably the drape is continuous across the interface portion and the bulk portion. It will typically be most convenient for the interface portion 602 to be within a bulk portion 601 in this manner so that the bulk portion 601 can extend away from the interface portion 602 so as to cover the robot arm. The bulk portion suitably comprises the plastic sheet.

Suitably the interface portion exhibits a different behaviour to the bulk portion when under stress, for example uniaxial stress or biaxial stress.

In FIG. 6a, the interface portion 602 is shown as being roughly rectangular. This shape is not critical. Generally it is preferable for the shape of the interface portion 602 to correspond to the shape of the drive assembly interface (or the projection of the drive assembly interface onto a plane).

The interface portion 602 is configured to accommodate movement of the drive assembly interface elements without the sterile barrier thereby being compromised. Thus, in one example, movement of the drive assembly interface elements can occur without causing a rip, tear and/or hole (or other rupture) in the drape.

The interface portion 602 can comprise a compliant portion. The compliant portion is configured to accommodate movement of the drive assembly interface elements and the instrument interface elements. The compliant portion accommodates such movement without the drape thereby becoming taut. Thus the likelihood that the sterile barrier provided by the drape will be compromised is reduced. This can ensure that the sterile barrier is maintained throughout a surgical procedure.

In one example, the interface portion 602 comprises sufficient material such that when the drape is captured between the instrument interface 500 and the drive assembly interface 400, the captured material is baggy and/or unconstrained. The baggy, loose or unconstrained material is suitably sufficient to allow for the full range of motion of the drive assembly interface elements without the drape material stretching (or stretching beyond a resilient limit), ripping and/or tearing. In other words, the interface portion 602 is arranged so that an excess of material is provided for capture. A portion of the excess, or unconstrained, material is able to move relative to the bulk portion of the drape. This allows the interface portion 602 of the drape to permit engagement between the drive assembly interface elements and the instrument interface elements without becoming taut. In this way the provision of an unconstrained interface portion 602 permits the desired movement of the drive assembly so as to transfer drive whilst maintaining the integrity of the sterile barrier.

The interface portion and the bulk portion of the drape can, in one example, comprise different materials or materials with different properties or characteristics. Suitably the interface portion of the drape comprises a material with a low modulus (for example an elastic or tensile modulus) or with a low friction coefficient, in at least one direction. Preferably the interface portion comprises a material with a low modulus or with a low friction coefficient in a plurality of directions. In some examples, a modulus or friction coefficient can be considered to be low if the value for the interface portion is lower than the value for the bulk portion. In some examples, a modulus or friction coefficient can be considered to be low if the value for the interface portion is lower than a predetermined threshold value. Suitably, at least one of the bulk portion and the interface portion is of a liquid-impermeable material, for example a sheet or film. The bulk portion and the interface portion may comprise differing materials, both of which are liquid-impermeable. Suitably the interface portion is of a material configured to deform under tension. The interface portion suitably comprises a material more easily deformed under tension than the material of the bulk portion. For example, the interface portion is of a material configured to stretch and/or shear under tension.

In one example, the interface portion is of a woven material, for example a closely woven material. Suitably the woven material is one or a combination of a polyester, polypropylene, polyethylene and polytetrafluoroethylene (PTFE) material. Suitably the density of the weave of the woven material is at least about 140 threads per inch, and preferably at least about 270 or about 280 threads per inch. The woven material can permit the interface portion 602 to shear. Tension in the interface portion can thereby be relieved by shear of the interface portion. By forming the interface portion from a material designed to shear, the shear can be achieved without the interface portion thereby ripping, tearing, or otherwise rupturing. Thus the sterile barrier can be maintained.

The interface portion can be formed from a resilient material, such as an elasticated material. The resilient material can comprise a material from the following group: an elastic, a rubber, a natural rubber, polyisoprene, an elastomer, polybutadiene, polychloroprene, butyl rubber, nitrile rubber, silicone rubber, a vinyl, and polyvinyl chloride. This can permit stretching in the material without the material thereby rupturing.

The drape can comprise, or can be coupled to, at least one tension sensor for sensing tension in the material of the interface portion. The tension sensor, or sensors, can be coupled to the control unit 309. The coupling can be by one or more of a wired and a wireless connection. The control unit 309 is suitably configured to receive one or more signal from the tension sensor and to determine the tension in the material of the interface portion in dependence on the received signal. During normal operation, tension in the material of the interface portion will generally be within a known range. Tension will increase and decrease in sections of the material in response to movement of the drive assembly interface elements. A plurality of tension sensors can be used to sense tension at a plurality of points of the material of the interface portion.

Tension at one or more points in the interface material can be determined for a given or known configuration of the one or more drive assembly interface elements. The configuration of the one or more drive assembly interface elements can be determined by the control unit 309. Suitably the control unit 309 comprises a look-up table comprising expected tension values for a range of configurations of drive assembly interface elements.

If the interface portion ruptures, the tension at at least one point will differ from the expected tension. The control unit may be configured to compare the detected or sensed tension with the expected tension. A difference, for example a difference above a threshold difference (which might be an absolute value, or a proportion of the tension value), between the detected tension and the expected tension can be used to detect a rupture in the interface portion. The threshold difference is suitably configurable, for example user configurable. The point and/or points at which the tension differs, or at which the difference is a maximum, can be used to determine the nature and location of the rupture. Based on this determination, the control unit can determine whether a surgical procedure is able to continue, or whether the rupture is such as to require attention before the surgical procedure can continue. Action, such as a visual inspection by an operator, can be indicated by the control unit.

The expected tension, or a reference tension, can be calculated by the control unit. The control unit can be configured to access a table, such as a look-up table. The table can comprise at least one reference tension for at least one configuration of the drive assembly interface elements. The expected or reference tension can be determined by the control unit in dependence on a reference to the table. For example the reference tension can be read out from the table according to the drive assembly interface element configuration, or the nearest such configuration in the table to the actual configuration, or a reference tension can be interpolated between reference tensions in the table, or extrapolated from reference tensions in the table. The control unit 309 may comprise the table. Suitably the memory 311 comprises the table. A tension may also be referred to as a force.

Figure 6B:
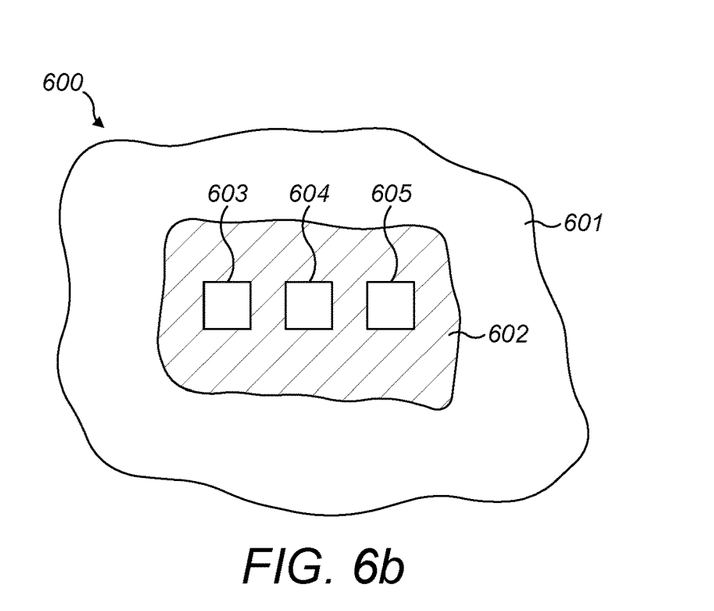
Figure 6C:
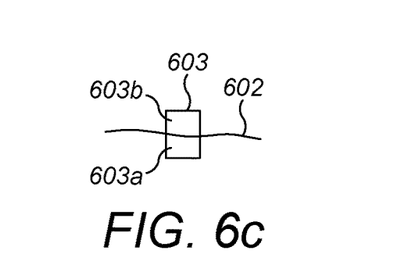

Referring now to FIG. 6b, the interface portion 602 can comprise at least one drive transfer element 603, 604, 605. Each drive transfer element is for transferring drive between the drive assembly interface element and the instrument interface element. Three drive transfer elements are illustrated in FIG. 6 to transfer drive between the drive assembly interface comprising three drive assembly interface elements and the instrument interface comprising three instrument interface elements. As discussed above, the drive assembly interface element and the instrument interface element may comprise one or other of a protrusion and a recess. Thus the drive transfer element suitably comprises a protrusion or recess for engaging with a recess or protrusion respectively on the drive assembly interface element and a protrusion or recess for engaging with a recess or protrusion respectively on the instrument interface element. Referring to FIG. 6c, the drive transfer element 603 may comprise a first portion 603a and a second portion 603b. The first portion 603a is suitably disposed to one side of the drape. The first portion 603a is engageable with the robot arm. For example, the first portion 603a is engageable with the drive assembly interface 400, such as being engageable with a drive assembly interface element. The second portion 603b is suitably disposed to the other side of the drape. The second portion 603b is engageable with the instrument. For example, the second portion 603b is engageable with the instrument interface 500, such as being engageable with an instrument interface element. The drive transfer element permits transfer of drive between the drive assembly interface 400 and the instrument interface 500.

The drive transfer element may be attached to the drape by sandwiching a portion of the drape 602 between the first portion 603a and the second portion 603b. Alternatively, the drive transfer element can be attached to the drape around a periphery of the drive transfer element, so that the drive transfer element extends to both sides of the drape. The drive transfer element, or the first and/or the second portion, can be attached to the drape in any convenient way, such as by at least one of welding, for example hot-gas welding, vibration welding, ultrasonic welding, induction welding, infrared/laser welding and dielectric welding, and bonding, for example by an adhesive, by solvent bonding or by fusion bonding.

In another example the interface portion 602, or the compliant portion of the interface portion, comprises one or more ruckle (or folding/wrinkling) control portions, or material control portions, for controlling the material in the region of the interface portion. The ruckle control portion reduces the likelihood that the material of the interface portion 602 ruckles (or folds/wrinkles) and/or controls the extent to which the material of the interface portion 602 ruckles. The ruckle control portion is arranged to control the manner in which material of the interface portion moves as the drive assembly interface elements move. This can permit control of, and/or reaction to, the tension within the material of the interface portion.

The ruckle control portion suitably interfaces between the drive assembly interface 400 and the instrument interface 500. The ruckle control portion may be integrally formed with the drape. Alternatively, the ruckle control portion may be formed separately from the drape and subsequently attached to the drape. Either way, the ruckle control portion is sterile. One side of the ruckle control portion directly contacts the drive assembly interface. The other side of the ruckle control portion directly contacts the instrument interface. Thus, the ruckle control portion prevents the non-sterile drive assembly interface from directly touching the sterile instrument interface and hence maintains the sterile barrier between the two components.

Figure 7A:
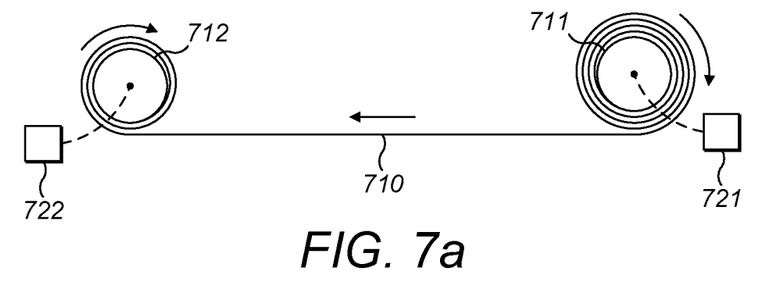
FIG. 7a schematically illustrates a side view of a ruckle control portion.
Figure 7B:
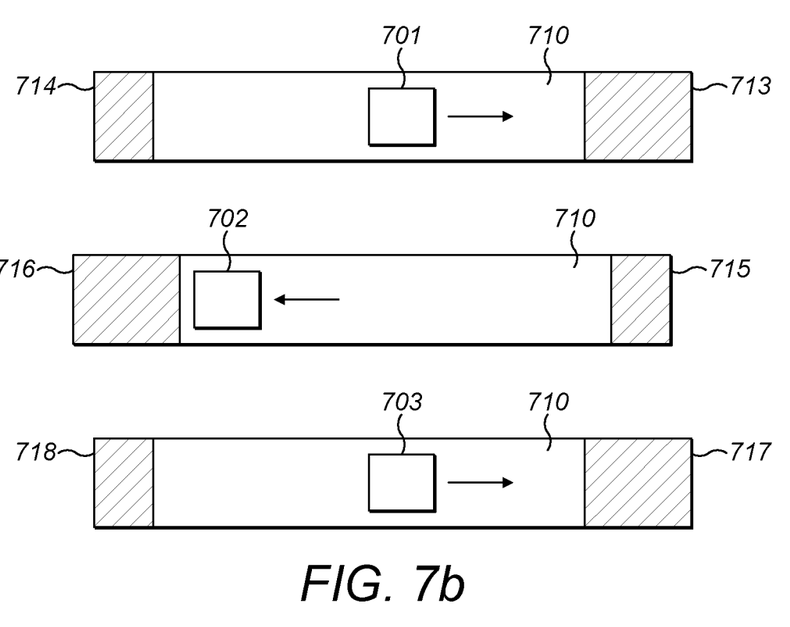

Referring to FIGS. 7a and 7b, the ruckle control portion comprises one or more movable portion 710. Suitably the movable portion is flexible and/or resilient, such as being elasticated. For example, the movable portion is a material such as a fabric. Preferably the material is water-resistant to assist in providing the sterile barrier between the robot arm and the instrument. The material can be constructed of a plastic sheet, for example made of polyester, polypropylene, polyethylene or polytetrafluoroethylene (PTFE). The movable portion 710 reduces the likelihood that the material of the ruckle control portion ruckles and/or controls the extent to which the material of the ruckle control portion ruckles. The movable portion is arranged to control the manner in which material of the ruckle control portion moves as the drive transfer elements move. This can permit control of, and/or reaction to, the tension within the material of the ruckle control portion.

In one example, the material of the movable portion 710 is captured between the drive assembly interface element and the instrument interface element. The movable portion is configured to move together with the movement of the drive assembly interface element, thereby avoiding ripping or tearing of the movable portion. In another example one or more drive transfer element is provided on or attached to the movable portion 710.

In the illustrated example, two reels 711, 712 are provided. Each reel is configured to hold and retain an amount of material. Material can be rolled onto one or both reels to take up slack in the material between the reels. Material can be rolled off one or both reels to relieve tension in the material between the reels. Material can be rolled onto or off the reels to accommodate movement of the drive assembly interface elements, and thereby of the drive transfer elements engaged to the drive assembly interface elements.

Referring to FIG. 7a, the material between the reels moves to the left. This is, for example, because the drive assembly interface element is driven to the left by the drive assembly. As the drive assembly interface element moves to the left, the movable portion will also move to the left. This is because it will be captured between the drive assembly interface element and the instrument interface element, or because a drive transfer element attached to the movable portion is engaged with the drive assembly interface element. The right-hand reel 711 will rotate clockwise, as indicted by the arrow, to feed material from the right-hand reel 711. This means that material between the drive assembly interface element and the right-hand reel 711 is not exposed to a high tension that might otherwise cause a rupture in the material, and/or disrupt operation of the ruckle control portion and/or the instrument interface. The left-hand reel 712 can rotate anti-clockwise, as indicated by the arrow, to roll material onto the left-hand reel 712. This means that material between the drive assembly interface element and the left-hand reel 712 does not become loose. Similarly, if the drive assembly interface element moves to the right, material will be fed from the left-hand reel 712. Material can be taken up by the right-hand reel 711. Either or both of the left-hand reel 712 and the right-hand reel 711 need not take up slack in the material. However, maintaining the material taut can assist in maintaining the sterile barrier.

Referring now to FIG. 7*b*, three movable portions 710 are provided adjacent one another. Each has attached thereto a drive transfer element 701, 702, 703, though in other examples one or more drive transfer element need not be provided. Three pairs of reels are provided. This permits the three movable portions to move independently of one another without such independent movement causing tension to increase in the material of the ruckle control portion. For example, the provision of a pair of reels for each movable portion can reduce the extent to which the material of the movable portion is exposed to tension, shear forces and/or rupture. This reduction may be in comparison to an arrangement in which a single pair of reels is provided for a plurality of movable portions, and the positioning of the material is based, for example, on an average such as a weighted average of the positions of the plurality of movable portions.

In the illustrated example, an uppermost (in the orientation of FIG. 7*b*) drive transfer element 701 is moved to the right (as indicated by the arrow), a middle drive transfer element 702 is moved to the left (as indicated by the arrow) and a lower drive transfer element 703 is moved to the right (as indicated by the arrow). A first right-hand reel 713, that of the uppermost section, takes up material of the movable portion and so has a greater reel diameter. A first left-hand reel 714, that of the uppermost section, feeds material of the movable portion from the reel and so has a smaller reel diameter. A second right-hand reel 715, that of the middle section, feeds material of the movable portion from the reel and so has a smaller reel diameter. A second left-hand reel 716, that of the middle section, takes up material of the movable portion and so has a greater reel diameter. A third right-hand reel 717, that of the lower section, takes up material of the movable portion and so has a greater reel diameter. A third left-hand reel 718, that of the lower section, feeds material of the movable portion from the reel and so has a smaller reel diameter.

It will be understood that where the number and/or arrangement of the movable portions differs from the illustrated example, the number and/or arrangement of the pairs of reels can similarly differ.

Material of the ruckle control portion, such as the movable portion, can be taken up and/or fed from a reel by driving the respective reel about its axis. Material of the ruckle control portion can be taken up and/or fed from a reel by resiliently biasing the respective reel about its axis. In one example each reel is resiliently biased and is also driven. Resiliently biasing a reel can assist in keeping tension within the material of the ruckle control portion consistent. When tension is lowered (by, for example, a drive transfer element moving towards the relevant reel), the biasing of the reel will cause the reel to rotate so as to take up material. When tension is increased (by, for example, a drive transfer element moving away from the relevant reel), the biasing of the reel will permit the reel to rotate so as to feed material from the reel. The resilience of the resilient biasing can be determined to provide for a desired tension or range of tension in the material of the ruckle control portion. The resilient biasing is, in one example, provided by a spring coupled to the respective reel.

Driving of the reels can be accomplished by coupling a motor, such as an electric motor, to each reel. Driving the reels can permit tension to be released and/or slack taken up at a desired speed. For example, driving the reels can permit tension to be released and/or slack taken up at a higher speed than might occur with resilient biasing. Driving the reels can permit tension to be controlled more accurately than by relying on resilient biasing, or on resilient biasing alone.

In one example, one of a pair of reels is coupled to a motor for driving that reel, and the other of the pair of reels is resiliently biased. The resilient biasing adapts to the tension in the material whilst the motor is driven so as to achieve a desired tension. This arrangement permits control of the tension in the material of the ruckle control portion.

A first tension sensor 721 (shown schematically in FIG. 7*a*) is coupled to the right-hand reel 711, 713, 715, 717. The first tension sensor is configured to sense tension in the material between the drive transfer element (or a portion of the movable portion captured between the drive assembly interface element and the instrument interface element) and the right-hand reel. The first tension sensor is suitably coupled to a rotational axis of the right-hand reel. A second tension sensor 722 (shown schematically in FIG. 7*a*) is coupled to the left-hand reel 712, 714, 716, 718. The second tension sensor is configured to sense tension in the material between the drive transfer element (or the portion of the movable portion captured between the drive assembly interface element and the instrument interface element) and the left-hand reel. The second tension sensor is suitably coupled to a rotational axis of the left-hand reel. Tension sensed by either or both of the first tension sensor and the second tension sensor is used to determine how to drive either or both of the right-hand reel and the left-hand reel. In other words, either or both of the right-hand reel and the left-hand reel is controlled in dependence on tension sensed by either or both of the first tension sensor and the second tension sensor.

The provision of the first tension sensor and the second tension sensor can permit a comparison of the tension sensed by each of the first and second tension sensors. This comparison can be used to detect rupture or other damage in the material. For example, if the tension sensed at both of a pair of reels reduces as a drive transfer element (or a movable portion) moves, it can be determined that the material between the reels has ruptured.

In some examples, only one tension sensor need be provided for each of a pair of reels.

Figure 8A:
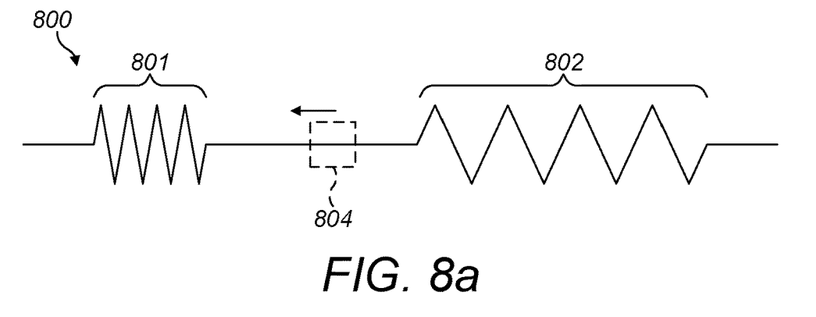
FIGS. 8a and 8b illustrates another ruckle control portion.
Figure 8B:
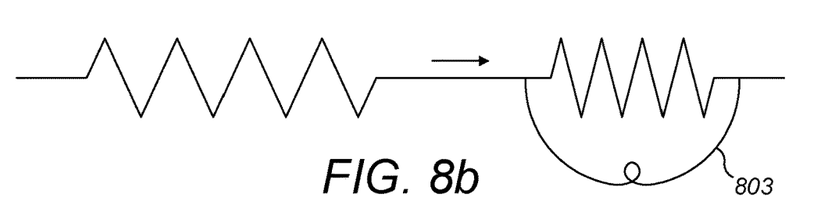

Another example of a ruckle control portion 800 is illustrated in FIGS. 8*a* and 8*b*. A first concertina section 801 and a second concertina section 802 are provided in the material of the interface portion, at locations spaced from one another. The drive assembly interface element and the instrument interface element capture a portion of the material between the concertina sections. Alternatively a drive transfer element 804 for engaging with the drive assembly interface element and the instrument interface element can be provided on the material between the concertina sections (as illustrated in FIG. 8*a* in dashed lines). Thus as the drive assembly interface element is driven, it will cause the material of the interface portion to move.

Each concertina section comprises a series of folds of material. The folds are at least one of pre-folded in the material and pre-stressed lines in the material. The concertina section has a contracted state in which the folds of material are relatively closer together, and an expanded state in which the folds of material are relatively further apart. As material of a concertina section is put under increased tension, for example by a drive assembly interface element moving away from the concertina section, the folds open up to permit movement of the material so as to restrict an increase in tension in the material. As material of a concertina section is put under reduced tension, for example by a drive assembly interface element moving towards the concertina section, the folds close up to permit movement of the material so as to restrict a decrease in tension in the material. The folds of the concertina section may be arranged to close up on a decrease in tension under a resilience of the material from which the folds are formed. Alternatively or additionally, a resilient member is coupled about a concertina section, for example by being coupled to material to either side of the concertina section, and configured to urge the concertina section towards a more folded configuration. An example of such a resilient member is a sprung element, as illustrated at 803 in FIG. 8*b*.

The concertina section can have an effective modulus (for example an elastic or tensile modulus) that is lower than that of the material from which it is formed. Forming the material into folds can reduce the overall modulus of the section. As a result, the concertina section is suitably expandable under a lower force than that required to expand a flat section of material from which the concertina section is formed.

In another example, the folds of the concertina section may be arranged to open up on a decrease in compression under a resilience of the material from which the folds are formed. Alternatively or additionally, a resilient member is coupled about a concertina section, for example by being coupled to material to either side of the concertina section, and configured to urge the concertina section towards a more expanded configuration. A sprung element of the type illustrated at 803 in FIG. 8*b* is an example of such a resilient member.

Referring to FIG. 8*a*, as a drive assembly interface element moves to the left (in the orientation of FIG. 8*a*), causing material of the interface portion to move to the left, as indicated by the arrow, the first concertina section 801 closes up, so that the folds of the first concertina section 801 become closer together; the second concertina section 802 opens up, so that the folds of the second concertina section 802 become further apart. Thus the material of the interface portion is able to move with the drive assembly interface elements without causing rupture of the material.

One ruckle control portion 800 can be provided to correspond to each drive assembly interface element. Thus where there are three drive assembly interface elements, three ruckle control portions 800 can be provided. The number and/or arrangement of the ruckle control portions 800 can differ as the number and/or arrangement of the drive assembly interface elements differ.

Whilst providing two concertina sections for each concertina ruckle control portion is preferable, in some examples, only one concertina section need be provided. In this case, tension can be accommodated by at least one of material stretch, material deformation and an unconstrained portion, or a loose portion, of material.

The concertina sections described above can accommodate linear movement. It is also possible to accommodate movement other than linear movement. For example, movement in an arc can be accommodated by the provision of a fan-shaped concertina section.

In some examples, the interface portion comprises a modified portion, permitting deformation of the interface portion preferentially in a predetermined way, as illustrated in FIGS. 9*a* to 9*d*. The modified portion 901 is thickened and/or strengthened. The modified portion 901 is thickened and/or strengthened relative to an unmodified portion 902 of the interface portion that is not thickened or strengthened. Thus the modified portion 901 is relatively thicker and/or stronger than the unmodified portion 902. In the example illustrated in FIG. 9*a*, two modified portions 901 are provided, one to either side of the unmodified portion 902.

Figure 9A:
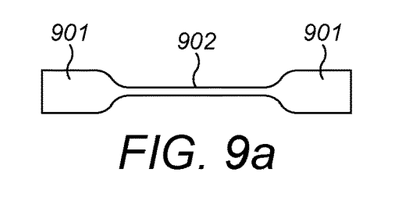
FIGS. 9a to 9d illustrate sections of an interface portion of a surgical drape.

The interface portion can be provided in sections, and at least one section can be provided with at least one modified portion 901. The modified portions can be provided at the periphery of the unmodified portion 902. In other words, the modified portions 901 can form edges to a section, the middle of which is an unmodified portion 902.

Figure 9B:
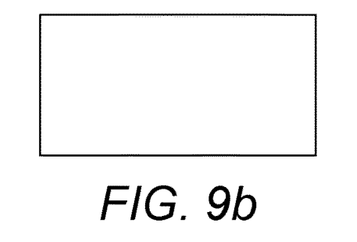

The modified portions 901 permit control of the deformation of the interface portion, for example when under tension and/or shear. In the illustrated example, when the section shown in FIG. 9*b* is subject to shear forces, it will preferentially shear in the manner shown in FIG. 9*c*. In one example, the force required to shear the unmodified portion 902 is less than the force required to cause the modified portions 901 along the two side edges of the illustrated section to bend. Thus the modified portions 901 along the two side edges of the illustrated section do not bend, but rather substantially retain their shape in a straight line, causing the material of the unmodified portion 902 to preferentially deform. In some examples the modified portions 901 do not extend all the way into each of the corners of a section to permit such deformation. Suitably the modulus of the section is lower than that of the bulk portion of the drape in at least one direction. Suitably the section preferentially deforms along this direction.

Figure 9C:
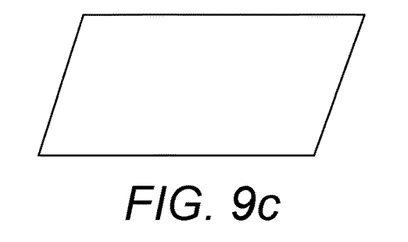

In other words, the modified portions 901 control the deformation of the section. Where there are a plurality of such sections, the modified portions 901 control the deformation of each section, and thereby the deformation of the interface portion.

Whilst the example illustrated is in the form of a quadrilateral, any other shape can be provided. In one example the section is hexagonally shaped. The modified portions 901 form the edges of the hexagon. More generally, the section can be polygonal in shape. The modified portions 901 form at least one of the sides of the polygon. In other examples it is desirable to provide the modified portions 901 in an arcuate shape, such as in a circular shape. A combination of two or more shapes is possible.

Figure 9D:
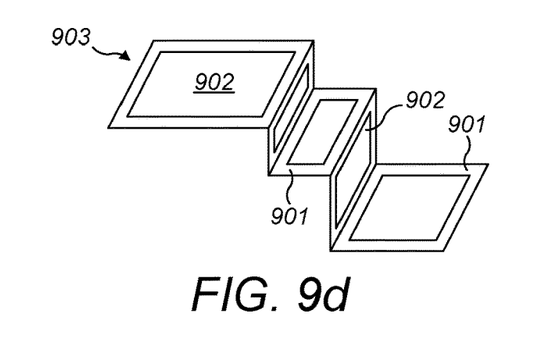

FIG. 9*d* illustrates an example in which several sections are provided adjacent one another. Each section is bounded by modified portions 901. Unmodified portions 902 are provided in the middle of each section. When the overall portion of material 903 is subject to tension, it will preferentially deform in the manner illustrated. Thus control of the deformation of the material can be achieved. This permits the interface portion to accommodate movement of the drive assembly interface element (which might either capture material of the interface portion against the instrument interface element, or engage with a drive transfer element provided on the interface portion), causing a change in tension in the material, without rupture.

Figure 10:
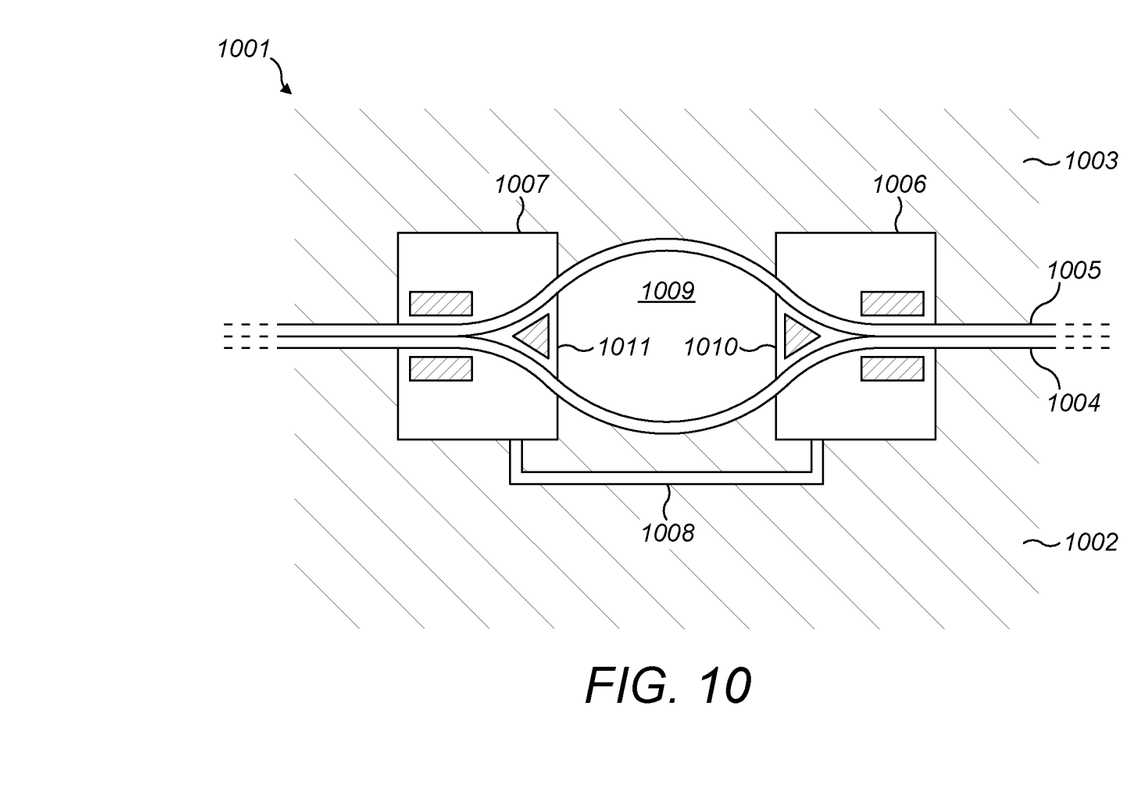
FIG. 10 illustrates joining devices of an interface portion.

In another example, illustrated in FIG. 10, the interface portion 1001 comprises a first drape portion 1002 and a second drape portion 1003. An edge of the first drape portion 1002 disposed towards the second drape portion 1003 comprises a first strip 1004. An edge of the second drape portion 1003 disposed towards the first drape portion 1002 comprises a second strip 1005. The first strip 1004 and the second strip 1005 comprise engagement portions for engaging with one another. The first drape portion and the second drape portion engage with one another along a joining line. The first strip 1004 and the second strip 1005 sealingly engage with one another. The first strip 1004 and the second strip 1005 sealingly engage with one another so as to maintain the sterile barrier. The first drape portion and the second drape portion are movable relative to one another (towards and away from one another) so as to open up a gap between them, and close the gap. In this way, at least one of the first drape portion and the second drape portion are movable relative to the bulk drape portion.

Suitably, the first strip 1004 comprises a first set of interlocking teeth. Suitably, the second strip 1005 comprises a second set of interlocking teeth. The first and second sets of interlocking teeth are configured to interlock with each other to permit controlled joining and separation of the first strip 1004 and the second strip 1005. This permits joining and separation of the first drape portion 1002 and the second drape portion 1003.

The interface portion 1001 comprises a first joining device 1006 and a second joining device 1007. Each joining device 1006, 1007 is able to join together the first strip 1004 and the second strip 1005 by causing the first and second sets of interlocking teeth to engage with one another. Each joining device 1006, 1007 is able to separate the first strip 1004 from the second strip 1005 by causing the first and second sets of interlocking teeth to disengage from one another. The first joining device 1006 is able to join the first and second strips when moving in a first direction relative to the first and second strips. The first joining device 1006 is able to separate the first and second strips when moving in a second direction relative to the first and second strips, generally opposite to the first direction.

The first joining device 1006 and the second joining device 1007 are arranged back-to-back. In this way, the second joining device 1007 is able to join the first and second strips when moving in the second direction, and is able to separate the first and second strips when moving in the first direction.

The joining devices are configured so that they separate the first and second strips 1004, 1005 in the region between the joining devices, and join the first and second strips 1004, 1005 together in regions to either side of the pair of the first and second joining devices. This is illustrated in FIG. 10.

The first and second joining devices 1006, 1007 are coupled together by a coupling element 1008. The coupling element suitably maintains the spatial relationship between the first and second joining devices 1006, 1007. In the illustrated example, the coupling element 1008 is a bar, but it will be understood that any other suitable form of coupling can be provided. It is also possible for there to be some tolerance in the maintenance of the spatial relationship of the first and second joining devices. In other words, the precise spatial relationship is not critical, but there may be a range of separation distances between the two joining devices. Thus the coupling element may have a resilience. For example, the coupling element may comprise a resilient portion. The resilience or resilient portion provides a desired tolerance in the spacing between the first and second joining devices.

A space or gap is maintained between the first and second joining devices 1006, 1007. Since the first and second strips 1004, 1005 are separated in the region between the first and second joining devices 1006, 1007, a gap or hole 1009 is formed in the interface portion in this region.

As the first joining device 1006 moves, the second joining device 1007 will be caused to move in the same direction as the first joining device 1006. The coupling element causes the movement of the first and second joining devices 1006, 1007 to be in the same direction.

Referring to FIG. 10, as the first and second joining devices move to the right (in the orientation of that figure), the first joining device 1006 will separate the first and second strips 1004, 1005. The second joining device 1007 will join together the first and second strips 1004, 1005. The gap 1009 is maintained between the regions in which the strips are joined together. Hence this gap moves together with the first and second joining devices 1006, 1007.

The interface portion is arranged so that the gap corresponds to the location and/or size of the protrusion of the drive assembly interface element or of the instrument interface element. The protrusion is therefore able to extend through the gap to engage with a corresponding recess in the instrument interface element or drive assembly interface element respectively. As the drive assembly interface element is driven, the protrusion will abut against a first inner edge 1010 of the first joining device 1006 or a second inner edge 1011 of the second joining device 1007. Movement of the protrusion will therefore cause movement of the pair of joining devices. Movement of the protrusion is therefore permitted whilst maintaining a sterile barrier around the protrusion.

The first and second joining devices are, in one example, zips. In another example, the first strip 1004 and the second strip 1005 are configured to engage with one another in a tongue-and-groove configuration.

The drape described herein could be used for non-surgical robotic purposes. For example, it could be used in robotic systems, or systems more generally, in which it is desirable to provide a barrier which permits motion feedthrough. Such a barrier might be a barrier to fluid flow and/or a barrier to particulate matter, for example particulate matter entrained in a flow of fluid such as air. Such a barrier can therefore be used to provide effective protection from chemicals, material filings and/or dust.

The applicant hereby discloses in isolation each individual feature described herein and any combination of two or more such features, to the extent that such features or combinations are capable of being carried out based on the present specification as a whole in the light of the common general knowledge of a person skilled in the art, irrespective of whether such features or combinations of features solve any problems disclosed herein, and without limitation to the scope of the claims. The applicant indicates that aspects of the present invention may consist of any such individual feature or combination of features. In view of the foregoing description it will be evident to a person skilled in the art that various modifications may be made within the scope of the invention.

The invention claimed is:

1. A surgical drape for covering at least a portion of a surgical robot arm, the arm comprising at least one drive assembly interface element for transferring drive between the arm and an instrument engageable with the arm, the drape comprising:
   an interface portion locatable between the arm and the instrument when the instrument is engaged with the arm, the interface portion comprising a drive transfer element engageable with the drive assembly interface element, a first drive transfer element portion disposed to one side of the drape, the first drive transfer element being engageable with the drive assembly interface element, a second drive transfer element portion disposed to another side of the drape, the second drive transfer element portion being engageable with an instrument interface element; and a bulk portion encompassing the interface portion;

the interface portion and the bulk portion being adjacent one another, the interface portion comprising a material or configuration having a lower modulus than that of the bulk portion in at least one direction, so as to permit repeatable movement of a portion of the interface portion relative to the bulk portion.

2. A surgical drape according to claim 1, in which the interface portion comprises a movable portion, the movable portion being movable relative to the bulk portion.

3. A surgical drape according to claim 1, in which the bulk portion wholly encompasses the interface portion.

4. A surgical drape according to claim 1, in which the material of the interface portion is at least one of a woven and a resilient material.

5. A surgical drape according to claim 1, in which the interface portion comprises an unconstrained portion of the drape.

6. A surgical drape according to claim 1, in which the interface portion comprises a ruckle control portion configured to at least partially control tension in the material of the drape.

7. A surgical drape according to claim 6, in which the ruckle control portion comprises the movable portion.

8. A surgical drape according to claim 6, in which the ruckle control portion comprises a concertina section, the concertina section being configurable between an expanded state and a contracted state.

9. A surgical drape according to claim 8, in which the concertina section is biased towards one of the expanded state and the contracted state.

10. A surgical drape according to claim 6, in which the ruckle control portion comprises a reel for at least one of winding on and unwinding material of the movable portion.

11. A surgical drape according to claim 10, in which the reel is at least one of biased and drivable in a rotary direction.

12. A surgical drape according to claim 6, in which the ruckle control portion comprises a strengthened portion, the strengthened portion being configured to permit a preferential deformation of the interface portion under action of a force.

13. A surgical drape according to claim 12, in which the strengthened portion forms at least part of a periphery of a non-strengthened portion.

14. A surgical drape according to claim 6, in which the drape is configured to engage with a plurality of drive assembly interface elements, and the drape comprises a ruckle control portion corresponding to each of the plurality of drive assembly interface elements.

15. A surgical drape according to claim 1, in which the movable portion comprises a first drape portion and a second drape portion, the first drape portion and the second drape portion being releasably engageable with one another along a joining line such that a gap between the first drape portion and the second drape portion is movable along the joining line.

16. A surgical drape according to claim 1, in which the drape comprises a sensor for sensing at least one of tension in the drape and force on the drape.

17. A surgical system comprising a surgical drape according to claim 1, a control unit and a sensor; the sensor being configured to sense at least one of tension in the drape and force on the drape and to transmit a signal to the control unit, and the control unit being configured to determine at least one of the tension in the drape and the force on the drape in dependence on the signal.

* * * * *